US008869585B2

(12) United States Patent
Troughton et al.

(10) Patent No.: US 8,869,585 B2
(45) Date of Patent: Oct. 28, 2014

(54) METHODS OF CALIBRATING A SENSOR IN A PATIENT MONITORING SYSTEM

(75) Inventors: Gavin Troughton, Cambridge (GB); Peter Laitenberger, Cambridge (GB)

(73) Assignee: Sphere Medical Limited, Cambridge, Cambridgeshire (GB)

( * ) Notice: Subject to any disclaimer, the term of this patent is extended or adjusted under 35 U.S.C. 154(b) by 583 days.

(21) Appl. No.: 12/918,311

(22) PCT Filed: Feb. 19, 2009

(86) PCT No.: PCT/GB2009/050161
§ 371 (c)(1),
(2), (4) Date: Nov. 10, 2010

(87) PCT Pub. No.: WO2009/104016
PCT Pub. Date: Aug. 27, 2009

(65) Prior Publication Data
US 2011/0120206 A1    May 26, 2011

(30) Foreign Application Priority Data

Feb. 19, 2008   (GB) .................................. 0802990.2

(51) Int. Cl.
*A61B 5/1495*   (2006.01)
(52) U.S. Cl.
CPC ....... *A61B 5/1495* (2013.01); *A61B 2560/0223* (2013.01)
USPC ............................................ 73/1.03; 73/1.88
(58) Field of Classification Search
USPC ................. 73/1.01, 1.02, 1.03, 1.88
See application file for complete search history.

(56) References Cited

U.S. PATENT DOCUMENTS

| 4,043,756 | A |   | 8/1977  | Sommervold           |
|-----------|---|---|---------|----------------------|
| 4,489,590 | A | * | 12/1984 | Hadden .......................... 73/1.04 |
| 4,912,417 | A | * | 3/1990  | Gibboney et al. ............. 324/438 |
| 5,207,087 | A |   | 5/1993  | Costello             |

(Continued)

FOREIGN PATENT DOCUMENTS

| EP | 0270-088 A1   | 6/1988 |
|----|---------------|--------|
| WO | WO 03/019165 A2 | 3/2003 |

(Continued)

OTHER PUBLICATIONS

Oberhardt et al., "Glucose Sensor Characteristics for Miniaturized Portable Closec-Loop Insulin Delivery", Diabetes Care, vol. 5, No. 3, May-Jun. 1982.*

*Primary Examiner* — David A Rogers
(74) *Attorney, Agent, or Firm* — Blakely Sokoloff Taylor & Zafman

(57) ABSTRACT

Methods and systems for calibrating a sensor for measuring an analyte in a patient monitoring system are disclosed. The method includes calculating sensor drift; calibrating the sensor using at least one calibration fluid; and periodically updating the sensor calibration based on the sensor drift calculation. The system adjusts a gas concentration in a fluid. The method in one of several variations includes providing a calibration fluid; setting the analyte concentration in the first fluid to a first concentration with an adjustment mechanism; measuring the first analyte concentration with the sensor; setting the analyte concentration in the first fluid to a second concentration; measuring the second analyte concentration with the sensor; and determining the calibration coefficients for the sensor from the measured first and second analyte concentrations. Some embodiments ensure that the period between recalibrations of the sensor is extended, thus reducing the number of disruptions to the sensor monitoring process.

8 Claims, 10 Drawing Sheets

(56) References Cited

U.S. PATENT DOCUMENTS

| | | | |
|---|---|---|---|
| 5,731,508 A * | 3/1998 | Slemeyer | 73/1.03 |
| 6,237,394 B1 * | 5/2001 | Harris et al. | 73/1.88 |
| 6,241,663 B1 | 6/2001 | Wu et al. | |
| 6,712,071 B1 * | 3/2004 | Parker | 128/204.21 |
| 7,221,567 B2 | 5/2007 | Otsuki et al. | |
| 7,610,142 B1 * | 10/2009 | Hoard et al. | 701/109 |
| 2002/0019707 A1 | 2/2002 | Cohen et al. | |
| 2002/0121126 A1 * | 9/2002 | Kouznestov et al. | 73/1.03 |
| 2003/0048203 A1 * | 3/2003 | Clary et al. | 340/945 |
| 2003/0155241 A1 * | 8/2003 | Lai et al. | 204/461 |
| 2004/0190813 A1 * | 9/2004 | Kopelman et al. | 385/12 |
| 2004/0256685 A1 * | 12/2004 | Chou et al. | 257/414 |
| 2005/0072690 A1 * | 4/2005 | Fyles et al. | 205/783 |
| 2006/0019327 A1 | 1/2006 | Brister et al. | |
| 2006/0155486 A1 | 7/2006 | Walsh et al. | |
| 2006/0271320 A1 * | 11/2006 | Kumar et al. | 702/87 |
| 2007/0203966 A1 | 8/2007 | Brauker et al. | |
| 2007/0213611 A1 * | 9/2007 | Simpson et al. | 600/365 |
| 2007/0299617 A1 | 12/2007 | Willis | |
| 2008/0036734 A1 * | 2/2008 | Forsblad et al. | 345/156 |
| 2008/0077345 A1 * | 3/2008 | Mueller et al. | 702/104 |
| 2008/0200789 A1 * | 8/2008 | Brister et al. | 600/347 |
| 2008/0277277 A1 * | 11/2008 | Mao et al. | 204/403.06 |
| 2009/0018426 A1 * | 1/2009 | Markle et al. | 600/365 |
| 2009/0063081 A1 * | 3/2009 | Xu | 702/107 |
| 2010/0045951 A1 * | 2/2010 | Martens et al. | 355/30 |
| 2010/0072064 A1 * | 3/2010 | Heller et al. | 204/403.14 |
| 2010/0081908 A1 * | 4/2010 | Dobbles et al. | 600/347 |
| 2010/0179409 A1 * | 7/2010 | Kamath et al. | 600/365 |
| 2010/0212583 A1 * | 8/2010 | Brister et al. | 118/35 |
| 2010/0230285 A1 * | 9/2010 | Hoss et al. | 204/415 |
| 2011/0190614 A1 * | 8/2011 | Brister et al. | 600/347 |
| 2011/0218414 A1 * | 9/2011 | Kamath et al. | 600/345 |

FOREIGN PATENT DOCUMENTS

| | | |
|---|---|---|
| WO | WO 2005/041766 A1 | 5/2005 |
| WO | WO 2006/085087 A2 | 8/2006 |
| WO | WO 2008/094077 A2 | 8/2008 |

* cited by examiner

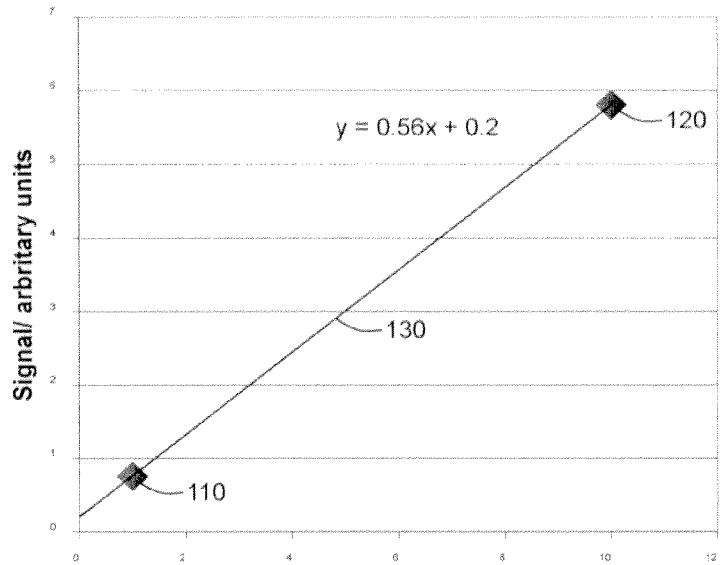
FIG. 1 – PRIOR ART
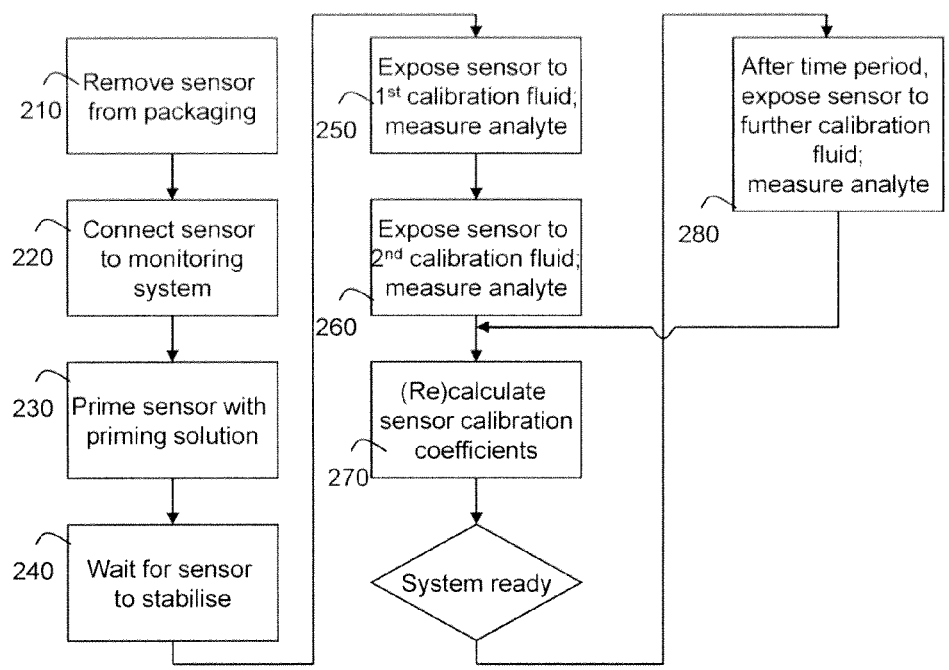
FIG. 2

METHODS OF CALIBRATING A SENSOR IN A PATIENT MONITORING SYSTEM

This is a non-provisional application claiming the benefit of International application number PCT/GB2009/050161 filed Feb. 19, 2009.

The present invention relates to methods of calibrating a sensor for measuring an analyte in a patient monitoring system.

Certain methods of medical treatment of patients may require the monitoring of the concentrations of one or more analytes in a bodily or other fluid of the patient, e.g. blood, urine or dialysate. Such analytes may comprise compounds dissolved in the fluid, e.g. gaseous compounds such as oxygen ($O_2$) or carbon dioxide ($CO_2$), or other types of dissolved compounds, e.g. electrolytes such as $Na^+$ and $K^+$, and glucose. In addition, such analytes may comprise compounds suspended in the fluid, e.g. red blood cells, whose volume fraction in the sample is characterised by a parameter called haematocrit.

To facilitate such monitoring, the patient may be connected to a monitoring system including one or more sensors for determining such analyte concentrations. This has the advantage that the analyte concentration can be monitored in a continuous manner. This reduces the risk that potential complications in the medical treatment of the patient are detected late. For example, the integration of a blood monitoring sensor in an extracorporeal circuit, such as a cardiopulmonary bypass (CPB) system, is beneficial because it allows the medical staff to readily obtain blood gas measurements without having to be exposed to blood extracted from the patient and without having to insert the extracted blood into a separate blood gas and electrolyte analyser, thus simplifying the monitoring process.

Many different types of such sensors are known. For example, WO99/17107 discloses a glucose sensor for such purposes. Many other examples will be readily available to the skilled person. In order for such a sensor to produce accurate readings of the analyte concentrations of interest, the output signal of the sensor has to be correlated to such analyte concentrations. This is generally carried out by passing one or more fluids containing known concentrations of the analyte of interest into the system and recording the sensor signal. By use of interpolation and extrapolation and taking into account the intrinsic response curve of the sensor, this may be used to construct a calibration curve of signal versus analyte concentration over the measurement range. When the signal from a sample is measured, the calibration curve is used to infer an analyte concentration.

FIG. 1 depicts a known way of calibrating a sensor by means of a two-point calibration. A first measurement point 110 is obtained from a first calibration fluid having a first analyte concentration and a second measurement point 120 is obtained from a second calibration fluid having a second analyte concentration. The slope and offset of the line 130 through these points provide the correlation of the sensor output with the analyte concentrations.

However, a known problem of such sensors is that the correlation between the sensor output and the analyte concentration changes over time due to changing conditions of the sensor, e.g. chemical changes or physical changes. For instance, amperometric sensors tend to exhibit a change in the slope of the line 130 over time, whereas potentiometric sensors tend to exhibit a change in the offset of the line 130 with the y-axis over time. Other types of sensors may exhibit similar drift behavior. Such changes in correlation are generally referred to as drift, and may be caused by slow degradation of the sensor.

Because of this drift behavior, such sensors need to be recalibrated periodically to ensure that the correlation between sensor signal output and analyte concentration remains within medical accuracy requirements. To this end, the sensors are typically exposed periodically to one or more calibration solutions having known analyte concentrations. In such a calibration procedure, the strength of the signal generated by the sensor, e.g. the sensor output voltage level, in response to the known concentrations is measured and correlated to the known concentrations to calibrate the sensor. An example of such a calibration method is shown in FIG. 2.

In step 200, a sensor is removed from its packaging, and connected to the patient monitoring system, e.g. a CPB system, in step 210. The sensor is primed with a priming fluid in step 220 and left to stabilize in step 230. Such a stabilization step typically comprises waiting until the sensor produces a stable output signal. This waiting step is depicted as step 240. In step 250, the sensor is exposed to a first calibration fluid, and a first measurement is taken. In step 260, the sensor is exposed to a second calibration fluid, and a second measurement is taken, after which the calibration coefficients of the sensor are calculated in step 270, after which the monitoring system is ready for use.

After a period of time, the sensor is exposed to at least one further calibration fluid in step 280, which may be the first calibration fluid, the second calibration fluid or another calibration fluid, after which the method reverts back to step 270 to recalculate the calibration coefficients of the sensor to compensate for any changes in the sensor response, such as drift in the sensor response occurring during the aforementioned period of time. Alternatively, step 280 may comprise a two-point recalibration measurement in which the sensor is exposed to the first calibration fluid and the second calibration fluid, respectively. The recalibration process is repeated during the active life of the sensor.

This approach has several disadvantages. For instance, it is difficult to ensure that the analyte concentrations in the calibration fluid are stable. This is especially the case when the analyte is a gas, e.g. $O_2$ or $CO_2$, having a non-ambient partial pressure in the fluid, in which case unexpected changes in the gas concentration may occur, e.g. when the calibration fluid is exposed to ambient conditions prior to inserting the calibration fluid into the sensor. Therefore, there remains a risk that the correlation obtained for a sensor calibrated with such a calibration fluid is inaccurate due to an unknown deviation in the analyte concentration in the calibration fluid.

Moreover, the recalibration of the sensor can be a complicated and relatively time-consuming process, during which the monitoring of the patient is interrupted because the sensor is exposed to one or more calibration fluids that have to be inserted into the sensor. It will be appreciated that such interruptions are undesirable, and their duration should be limited as much as possible.

The present invention seeks to provide several methods for calibrating a sensor as recited in the opening paragraph that overcome at least some of the aforementioned disadvantages.

In accordance with a first aspect of the present invention, there is provided a method of calibrating a sensor for measuring an analyte in a patient monitoring system, the method comprising calculating a sensor drift; calibrating the sensor using at least one calibration fluid; and periodically updating the sensor calibration based on the sensor drift calculation. This method is based on the realisation that the drift rate of a sensor is predictable, i.e. well-defined, over a prolonged period of time. Such predictable behaviour may include a constant, i.e. time-independent, drift rate as well as a predictable time-dependent drift rate. This realisation can be used to significantly reduce the amount of time required to recalibrate a sensor, because the sensor does not need to be exposed to calibration fluids during the recalibration process. This simplifies the task load of the operator of the sensor during its monitoring use.

The prolonged period of time may span the active life of the sensor. Alternatively, the active life of the sensor may comprise several time frames, with the sensor exhibiting respective predictable drift rates during the respective time frames. In this case, the aforementioned method may be repeated for each time frame.

The drift rate of the sensor may be estimated in a number of ways. In an embodiment, the method of the present invention further comprises providing the sensor with a first fluid comprising a predetermined concentration of an analyte; performing a first measurement of the analyte concentration in the first fluid with the sensor; and performing at least one additional measurement of a further predetermined analyte concentration in a further fluid, which may be the first fluid, with the sensor after a predetermined time period; and wherein the step of calculating the sensor drift comprises calculating said drift from the difference, if any, between the first measured analyte concentration and the further measured analyte concentration. Different fluids may be used as long as the analyte concentrations of both fluids are known.

In an advantageous embodiment, the first fluid and the further fluid are the same fluid. Hence, by keeping the concentration of an analyte constant over a period of time, any variation between two sensor measurements at the beginning and the end of the time period respectively provides a direct indication of the drift rate of the sensor.

In an embodiment, the patient monitoring system may comprise means for adjusting a gas concentration in the system, and wherein the analyte is said gas, the method further comprising maintaining a well-defined concentration of the gas in the first fluid, and if applicable, the further fluid, with said means for adjusting a gas concentration during the first measurement and the at least one additional further measurement. Such means, e.g. an oxygenator or a gas exchanger, can be used to ensure that the gas concentration in the first (and further) fluid is kept constant, or at least at a well-defined concentration. This facilitates using the blood of the patient as the first fluid, which further reduces the time required for calibrating the sensor, and increases the accuracy of the analyte concentrations when using non-ambient gas concentrations. The gas may comprise oxygen, carbon dioxide, other gases or a mixture of these gases.

In an alternative embodiment, the sensor is arranged to determine the analyte concentration in a flowing sample, the method further comprising the step of maintaining the first fluid stationary over the sensor during a time period including the first measurement and the second measurement. Any variation in the two sensor measurements can again be used to determine a drift rate of the sensor. This embodiment may also be used for a sensor that comprises means for altering the analyte concentration, e.g. a sensor comprising analyte consuming means such as an enzyme layer for consuming the analyte, an oxygen sensor, an amperometric sensor and so on, or means that allow an analyte concentration to change in a well-defined manner, e.g. certain types of membranes or materials allowing diffusion of the analyte into and out of the sensor. In this case, the step of calculating the drift comprises determining said drift based on a difference between the first measurement and the second measurement and a deviation of said difference from a predicted difference based on the known analyte consumption rate of said analyte consuming means.

In another embodiment, the method further comprises the step of stabilising the sensor with a priming fluid, said priming fluid comprising a first predetermined concentration of the analyte, and wherein the first fluid comprises the priming fluid; and the first analyte concentration and the second analyte concentration are determined during said stabilising. This embodiment is based on the realisation that the sensor drift rate during the sensor stabilisation process is indicative of the drift rate of the sensor during its active life. By performing the drift rate estimation during the stabilisation process, the additional time required for the calibration process is greatly reduced.

In yet another embodiment, the step of calculating a sensor drift is performed during manufacturing of the sensor. This has the advantage that calibration of the sensor may be performed with a single calibration fluid, after which the drift rate estimation data determined during the manufacturing process may be fed to the sensor instead of exposing the sensor to a second calibration fluid, thus reducing the time required for the calibration, and the recalibration in particular. It is reiterated that the drift rate estimation data may comprise data for several drift rate time frames, as previously explained. It is further reiterated that during a single one of such time frames, the drift rate is predictable, i.e. is constant or displays well-defined time-dependent behaviour.

During calibration of the sensor, the calibration readings may be used to normalise or adjust the (time-dependent) drift behaviour equations of the sensor determined during the manufacturing process. For instance, the general time-dependent behaviour of the sensor drift may be determined during manufacturing, with the (initial) calibration measurement(s) being used to provide fitting constants for the function capturing this general time-dependent behaviour. For example, in case of time-dependent drift behaviour captured by the general formula $A*\exp(t/T)$, the constants $A$ and $T$ may be determined during initial calibration, e.g. by means of a multipoint calibration, with t being a variable expressing elapsed usage of the sensor in an appropriate unit (e.g. minutes).

In an embodiment, the sensor may be provided with a fluid comprising a relatively constant analyte concentration over time to determine whether or not the sensor needs recalibration. This would be signaled by the occurrence of drift in the sensor readings. Such a fluid may be provided as a continuous flow over the sensor, or by providing a stationary fluid over the sensor for a period of time, e.g. by disruption a fluid flow over the sensor for this period.

According to a further aspect of the present invention, there is provided a method of calibrating a sensor for measuring an analyte in a patient monitoring system including means for adjusting the analyte concentration, the method comprising providing a calibration fluid; setting the analyte concentration in the first fluid to a first concentration with said adjusting means; measuring the first analyte concentration with the sensor; setting the analyte concentration in the first fluid to a second concentration with said adjusting means; measuring the second analyte concentration with the sensor; and determining the calibration coefficients for the sensor from the measured first analyte concentration and the measured second analyte concentration. By adjusting the analyte concentration of a fluid for calibrating the sensor in-situ, the calibration process can be performed more quickly and with less risk of analyte concentrations deviating from their intended values.

In an embodiment, the method further comprises the steps of periodically setting the analyte concentration in the first fluid to a further concentration with said adjusting means; measuring the further analyte concentration with the sensor; and adjusting the calibration coefficients for the sensor based on the measured further analyte concentration. This also reduces the time required for periodically recalibrating the sensor, which means a shorter disruption of the patient monitoring process.

The analyte may be a gas, such as $O_2$, $CO_2$, other gases or a mixture thereof, in which case the adjusting means may comprise an oxygenator. Alternatively, the system may comprise a shunt line, said sensor being located in the shunt line, and wherein the shunt line is coupled to adjusting means such as a gas cylinder.

According to yet another aspect of the present invention, there is provided a method of calibrating a sensor for measuring an analyte in a patient monitoring system, the method comprising exposing the sensor to a first fluid comprising a first unknown concentration of the analyte; measuring the first unknown analyte concentration with the sensor; determining the first unknown analyte concentration with an analyser external to the patient monitoring system; providing the sensor with the determined first analyte concentration, and determining the calibration coefficients for the sensor from the measured first unknown analyte concentration and the analyte concentration determined by the analyser.

In an embodiment, the method further comprises exposing the sensor to a second fluid having a further concentration of the analyte, measuring the further analyte concentration with the sensor; and wherein the determining step comprises determining the calibration coefficients for the sensor from the measured first unknown analyte concentration, the analyte concentration determined by the analyser and the measured further analyte concentration.

The further concentration may be a further unknown concentration, in which case the method further comprises determining the further unknown analyte concentration with an analyser, providing the sensor with the determined further analyte concentration and wherein said calibration coefficients determining step comprises determining the calibration coefficients for the sensor from the measured first unknown analyte concentration, the measured further unknown analyte concentration and the respective analyte concentrations determined by the analyser.

By using one or more calibration fluids having an unknown analyte concentration, and determining these concentrations on a separate analyser such as a blood gas and electrolyte analyser, fluids may be used for dual purposes. For instance, the first fluid may be a fluid for priming the sensor, and the second fluid may comprise the blood of the patient. This obviates the need to apply separate calibration solutions, thus reducing the time required for (re)calibration of the sensor, and improving the accuracy of the determined analyte concentrations, and the determined rift rate of the sensor as a consequence. The above calibration procedure may be periodically repeated for recalibration purposes.

Embodiments of the invention are described in more detail and by way of non-limiting examples with reference to the accompanying drawings, wherein:

FIG. 1 depicts a known method of correlating a sensor;

FIG. 2 depicts a flowchart of a known method of correlating a sensor;

It should be understood that the Figures are merely schematic and are not drawn to scale. It should also be understood that the same reference numerals are used throughout the Figures to indicate the same or similar parts.

It should also be understood that in the context of the present application, the term 'sensor' should not be construed to be limited to a device comprising a single sensing element; sensor devices comprising multiple sensing elements are also intended to be covered by phrase 'sensor' in this application. The phrase 'sensor' is further intended to cover a sensor in isolation, as well as a sensor including its control hardware, e.g. a bedside monitor or other suitable means for controlling such a sensor.

The methods of the present invention are particularly suitable for calibrating a sensor having a flow cell and being placed in a shunt line of the patient monitoring system. Such a shunt line is, for example, used to avoid exposing the sensor to the main arterial blood flow of the patient, since such exposure should, inter alia, be avoided for safety reasons. However, it should be understood that the methods of the present invention are not limited to flow cell-type sensors, and are not limited to sensors in shunt lines or to sensors operating in arterial blood. Other types of sensors in other configurations may be equally feasible for calibration by the methods of the present invention.

It should further be understood that although the present invention will be described in the context of calibrating a sensor in a CPB monitoring system, the present invention may also be used to calibrate a sensor in other extracorporeal monitoring systems, and in particular continuous monitoring systems, e.g. a continuous monitoring system for monitoring a diabetes patient, a continuous monitoring system for monitoring a patient under a global anesthetic, and so on.

Figure 3:
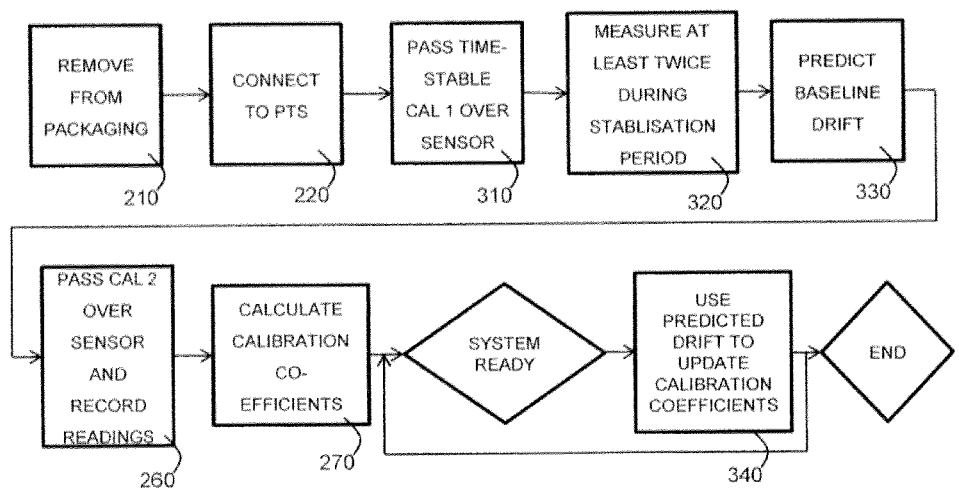
FIG. 3 depicts a flowchart of a method of correlating a sensor in accordance with an embodiment of the present invention.

FIG. 3 shows a first embodiment of a method of calibrating a sensor for measuring an analyte in a patient monitoring system, wherein the method comprises calculating a sensor drift; calibrating the sensor using at least one calibration fluid; and periodically updating the sensor calibration based on the sensor drift calculation.

In FIG. 3, the steps 210 and 220 may be the same as in FIG. 2. In step 310, a calibration fluid, e.g. a priming fluid, having a known analyte concentration which is stable, or at least well-defined over time is fed over the sensor for priming the sensor. Such priming is for instance necessary when the sensor is kept in a dried form on the shelf to prolong its lifetime. During the stabilisation process, two measurements of the known analyte concentration are performed with the sensor in step 320 whilst the sensor output is stabilising. The two measurements are separated by a predefined time period $\Delta t$. The two measurements are used in step 330 to calculate a drift rate D(t) of the sensor using an appropriate calculation method, for example:

$$D(t) = \frac{[c2] - [c1]}{\Delta t}$$

wherein [c1] and [c2] are the measured sensor signals to be correlated to the known concentrations in the first and second measurement respectively. The above formula is suitable for the calculation of a constant drift rate. In order to establish a time-dependent drift rate, one or more measurements may be used to extrapolate the time-dependent drift rate, for example by adjusting a time-varying function based on the results of these measurements or by using a more involved formula in which the time-dependency is factored into the equation.

The method may continue with a step 260 during which the sensor is exposed to a second calibration fluid on which a measurement is performed, after which the calibration coefficients are calculated for the sensor in step 270. The drift rate and the calibration coefficients may also be calculated at the same time, e.g. during step 270.

The system is now ready for monitoring the patient e.g. for a time period during which the sensor drift is deemed to remain within acceptable limits, after which the sensor needs recalibrating to compensate for this drift. In accordance with the method of the present invention, the sensor drift is not determined by exposing the sensor to further calibration fluids, but by using the drift parameters estimated in step 330 to update the calibration coefficients of the sensor in step 340.

This update process may be repeated as long as the drift parameters, e.g. the drift rate, remain constant, or at least well-defined enough. Whether or not the drift parameters remain well-defined during a predefined time frame is typically determined either prior to integrating the sensor in a patient monitoring system or from observations of the sensor response during use. In case it can be expected that the actual sensor drift parameters have deviated from the drift parameters estimated in step 330, e.g. after several calibration coefficient updates in step 340, the method may revert back to step 250 to update the estimated drift parameters.

Figure 4:
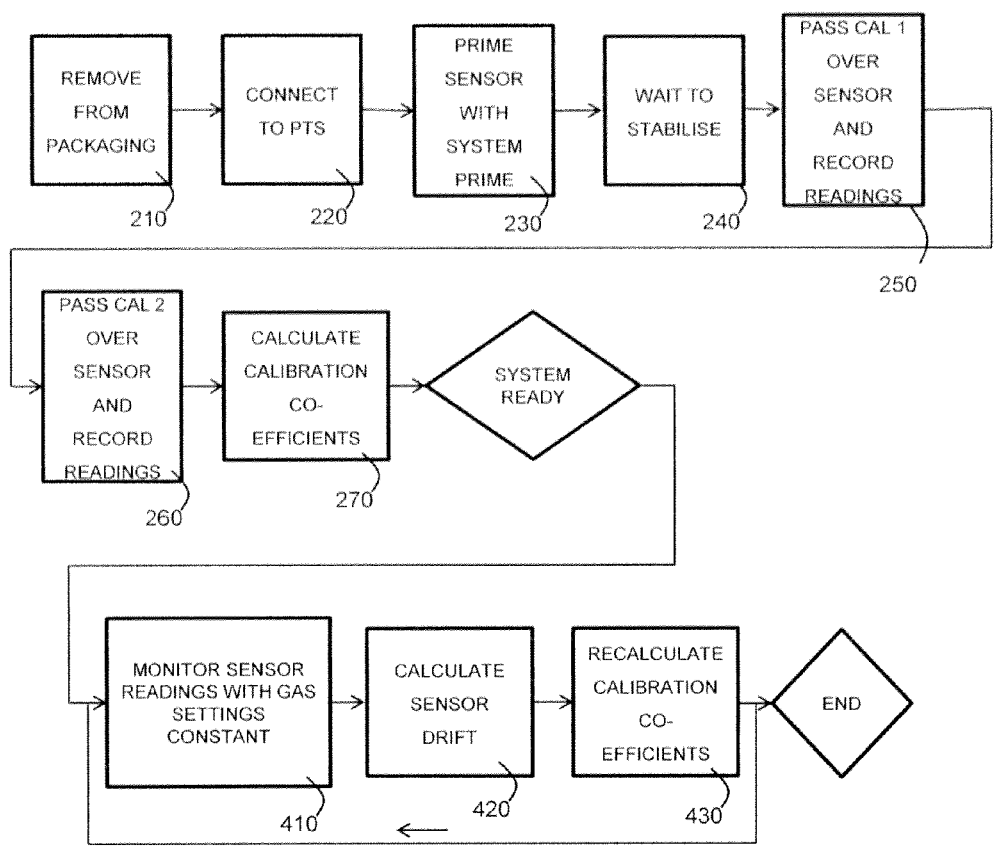
FIG. 4 depicts a flowchart of a method of correlating a sensor in accordance with another embodiment of the present invention.

FIG. 4 shows an alternative embodiment of the present invention. The initial calibration of the sensor may be performed in any suitable way, e.g. as depicted in steps 210-270 of the known method of FIG. 2.

In this embodiment, the system further comprises means for adjusting a gas concentration in a fluid, e.g. an oxygenator in a CPB set-up for replacing $CO_2$ in the patient's blood with $O_2$, a gas supply used in conjunction with a tonometer, or any other gas supply capable of maintaining a well-defined gas concentration, i.e. partial pressure, in a fluid. The sensor in this embodiment includes a means for measuring the partial pressure or concentration of such a gas, e.g. $pO_2$, or $pCO_2$, with the calibration fluids used in steps 250 and 260 comprising predefined partial pressures of the gas as the analyte of interest.

After a period of time has lapsed following the calibration of the sensor, the sensor may require recalibration. To this end, a fluid, which preferably is the patient's blood, is fed over the sensor in step 410 while the means for adjusting the gas concentration in the fluid are configured to ensure that the gas concentration is kept constant. The sensor performs two measurements of the fluid for determining the partial pressure of the gas concentration kept constant by said adjusting means. The two measurements are separated by a predefined time period, which can be utilised to calculate the sensor drift in step 420. The sensor drift may be calculated in substantially the same manner as in step 330 of FIG. 3.

The calculated drift is used to recalibrate the sensor in step 430 by recalculating the calibration coefficients of step 270 based on the calculated drift, after which the system can be used again for monitoring the patient. It will be understood that for this drift calculation to be very accurate, the adjustment means must be supplied with a constant gas supply, e.g. from a gas cylinder, and must maintain an efficient gas exchange over the period of time in which the sensor measurements are performed.

Figure 5:
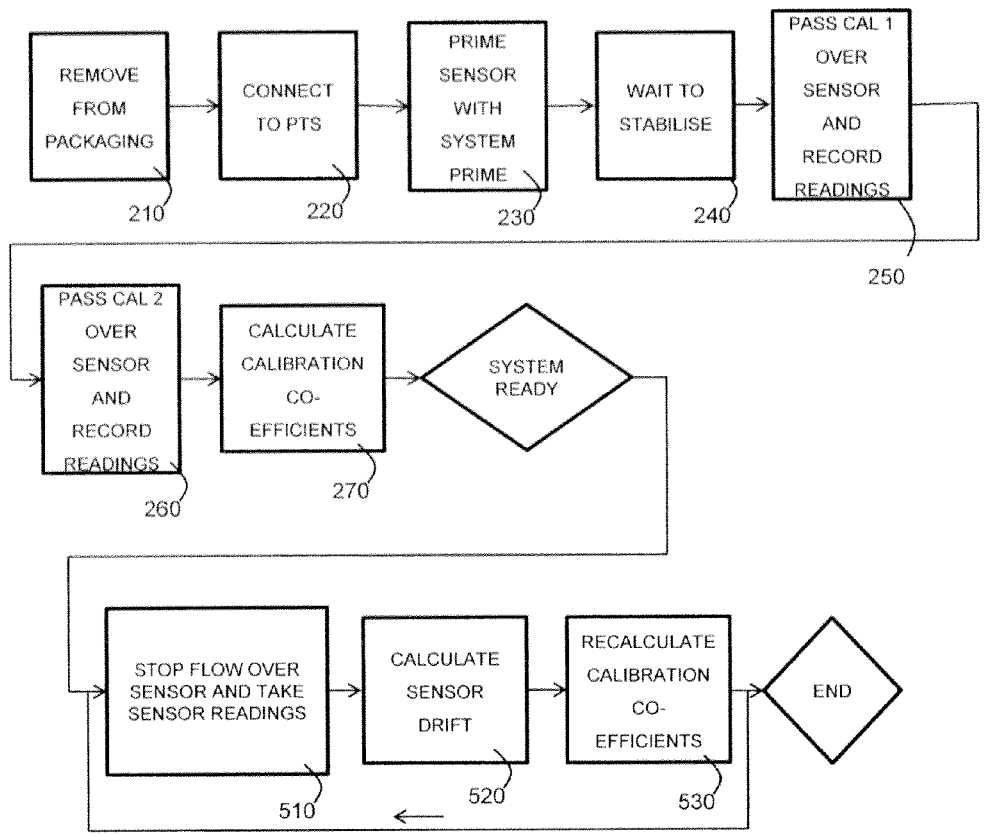
FIG. 5 depicts a flowchart of a method of correlating a sensor in accordance with yet another embodiment of the present invention.

A further embodiment of this method is shown in FIG. 5. This embodiment is particularly suitable for recalibrating sensors that measure an analyte in a fluid flowing over the sensor. In this embodiment, the initial calibration of the sensor may be carried out in any suitable way, e.g. as depicted in steps 210-270 of the known method of FIG. 2. As soon as the sensor requires calibrating, the sensor is provided with a fluid having a known analyte concentration in step 510. The fluid flow is stopped after which the sensor performs two measurements of the fluid for determining the analyte concentration in the fluid. Alternatively, the second measurement is performed using a different fluid having a further predefined analyte concentration. This does not require stopping the flow. The two measurements are separated by a predefined time period, which can be utilised to calculate the sensor drift in step 520. The sensor drift may be calculated in substantially the same manner as in step 330 of FIG. 3. The calculated drift is used to recalibrate the sensor in step 530 by recalculating the calibration coefficients of step 270 based on the calculated drift, after which the system can be used again for monitoring the patient.

It is pointed out that the sensor may comprise means for altering the analyte concentration, e.g. means that consume the analyte, such as an enzyme layer, an oxygen sensor, an amperometric sensor and so on, or means that allow analytes to enter or leave the fluid in the sensor area, e.g. certain types of membranes or materials. In this case, the step of calculating the drift comprises determining said drift based on a difference between the two measurements and a deviation of said difference from a predicted difference based on the known analyte consumption rate of said altering means.

Figure 6:
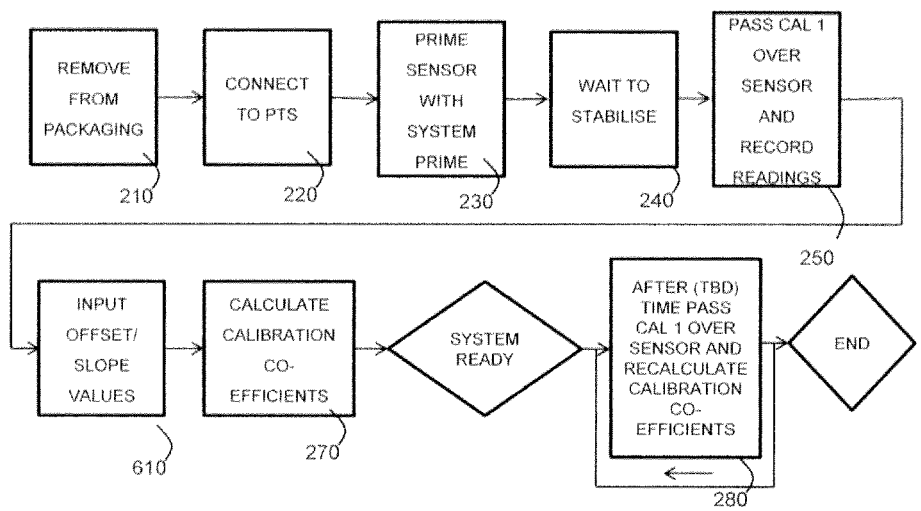
FIG. 6 depicts a flowchart of a method of correlating a sensor in accordance with yet another embodiment of the present invention.
Figure 7:
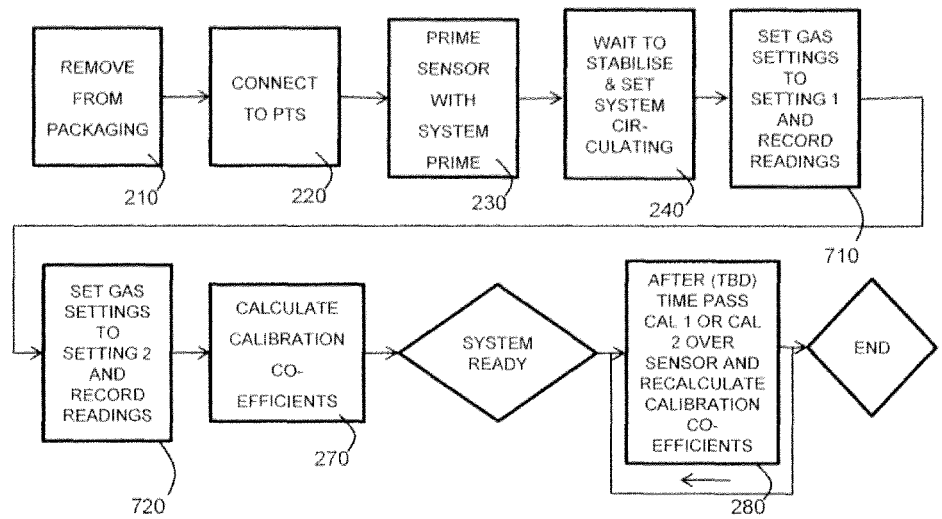
FIG. 7 depicts a flowchart of a method of correlating a sensor in accordance with yet another embodiment of the present invention.

Another embodiment of this method is shown in FIG. 6. In this embodiment, the sensor performs a first calibration measurement on any suitable calibration fluid. For instance, such a first calibration measurement procedure may comprise at least some of the steps 210-250 of the known method shown in FIG. 2. In step 610, the sensor is further provided with drift parameters that are determined during the manufacturing of the sensor. Such drift parameters may have been determined in any suitable way, e.g. by means of any of the methods depicted in FIGS. 3-5. The drift rate parameters may include a drift model that captures the time-dependent drift rate behavior.

The calibration measurement performed in step 250 and the drift parameters provided in step 610 are used to calculate the calibration coefficients in step 270. The sensor may be recalibrated in any suitable way, e.g. by passing one or more calibration fluids having a known analyte concentration over the sensor in step 280 and measuring this analyte concentration with the sensor, after which the sensor may be recalibrated based on this measurement.

Figure 8:
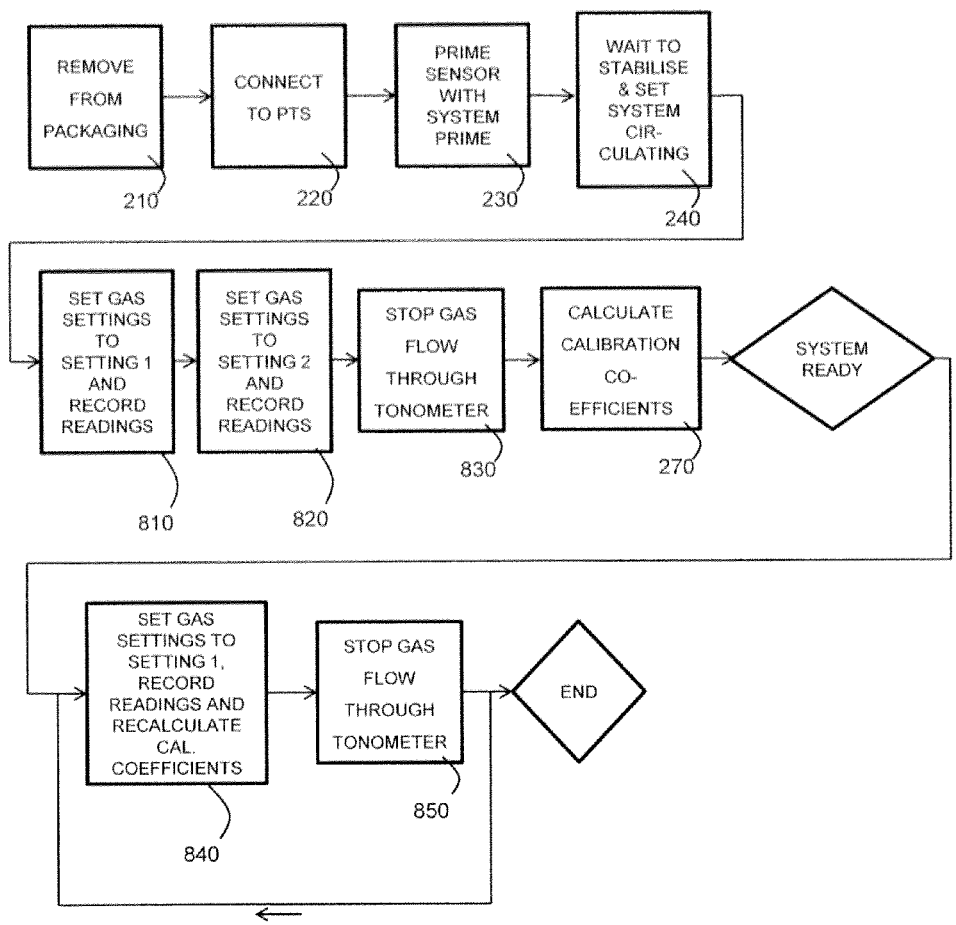
FIG. 8 depicts a flowchart of a method of correlating a sensor in accordance with yet another embodiment of the present invention.
Figure 9:
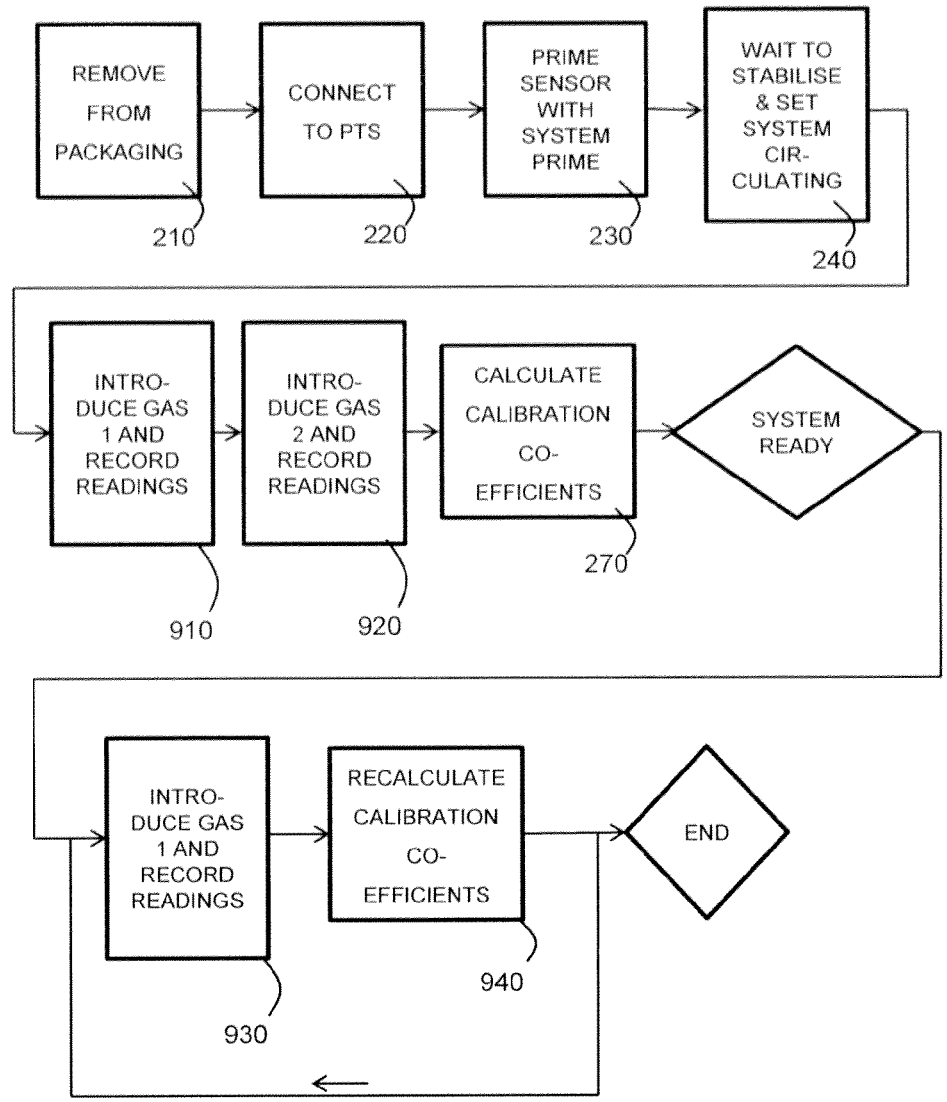
FIG. 9 depicts a flowchart of a method of correlating a sensor in accordance with yet another embodiment of the present invention.

Various embodiments of a method of calibrating a sensor for measuring an analyte in a patient monitoring system in accordance with a further aspect of the present invention are depicted in FIGS. 8 and 9. In these embodiments, the patient monitoring system includes means for adjusting the analyte concentration, e.g. analytes, such as dissolved gases. Such adjusting means may comprise an oxygenator in a CPB set-up for replacing $CO_2$ in the patient's blood with $O_2$, a gas supply used in conjunction with a tonometer, or any other gas supply capable of maintaining a well-defined gas concentration, i.e. partial pressure, in a fluid. The sensor in this embodiment may comprise a sensor for measuring the partial pressure of such a gas, e.g. $pO_2$, or $pCO_2$.

This method comprises the steps of calibrating a sensor for measuring an analyte in a patient monitoring system including means for adjusting the analyte concentration, the method comprising providing a calibration fluid; setting the analyte concentration in the first fluid to a first concentration with said adjusting means; measuring the first analyte concentration with the sensor; setting the analyte concentration in the first fluid to a second concentration with said adjusting means; measuring the second analyte concentration with the sensor; and determining the calibration coefficients for the sensor from the measured first analyte concentration and the measured second analyte concentration.

In FIG. 8, a sensor is provided and stabilised in any suitable way, such as by means of steps 210-240 as shown in FIG. 2 depicting the known calibration method. In FIG. 8, the adjusting means comprise a gas exchanger coupled to the monitoring system via a tonometer. In step 810, the adjusting means, set a concentration of an analyte in a first fluid, e.g. $pO_2$ or $pCO_2$, to a first predefined value, after which the sensor performs a first measurement of the first analyte concentration. In step 820, the adjusting means, set a concentration of the analyte in the first fluid to a second predefined value, after which the sensor performs a second measurement of the first analyte concentration. Subsequently, the gas flow through the tonometer is stopped in step 830. The first and second concentrations as determined by the sensor and the predefined first and second concentration values may be used to determine the calibration coefficients of the sensor in any suitable way, e.g. by means of step 270 of the known method depicted in FIG. 2.

An important advantage of this method is that a two-point calibration of the sensor may be performed using a single fluid by in-situ modification of the analyte concentration of the fluid. This reduces the time required for the calibration. In an embodiment, the fluid is the patient's blood. This further reduces the time required for the calibration because there is no need to supply the sensor with a separate calibration fluid. Alternatively, the fluid may be the fluid used for priming the sensor in step 230.

The sensor may also be recalibrated in this manner. To this end, after the monitoring system has been used for a predetermined period of time, e.g. a period of time during which the sensor is known to exhibit negligible, or at least well-defined drift only, the adjusting means are used to set the analyte concentration in the fluid to a further predetermined concentration, e.g. the first or second predetermined concentration, in step 840, after which the sensor performs a further measurement of the analyte concentration. Alternatively, rather than altering the concentration of the first fluid, further fluids may be used as long as the analyte concentrations in these fluids are well-defined. Subsequently, the gas flow through the tonometer is stopped in step 850. The further measurement and the further predetermined concentration are used to recalibrate the sensor in any suitable way. It will be appreciated that step 830 may be extended to a recalibration based on a two-point measurement.

The alternative embodiment of this method shown in FIG. 9 is particularly suitable for calibrating a sensor placed in a shunt line. The sensor may be stabilised in any suitable way, e.g. by means of steps 210-240 of the known method depicted in FIG. 2. In step 910, a first gas concentration is introduced into the shunt line, after which the sensor performs a measurement of the first gas concentration. In step 920, a second gas concentration is introduced into the shunt line, after which the sensor performs a measurement of the second gas concentration. It will be appreciated that in this embodiment, the fluid may be a gas mixture comprising a gaseous analyte of interest in a predefined concentration. It has been found that many sensors for measuring gas analytes can also accurately determine a gas concentration in such a gaseous fluid as long as the sensor remains properly primed.

In a next step, the first and second gas concentrations as determined by the sensor and the predefined first and second gas concentration values are used to determine the calibration coefficients of the sensor in any suitable way, e.g. by means of step 270 of the known method depicted in FIG. 2.

The sensor may also be recalibrated in this manner. In step 930, a gas mixture comprising a predefined concentration of the analyte of interest is introduced into the shunt line, after which the sensor measures the concentration of the analyte of interest, after which the calibration coefficients of the sensor may be updated in step 940. It will be appreciated that steps 930 may be extended to a recalibration based on a two-point measurement.

Figure 10:
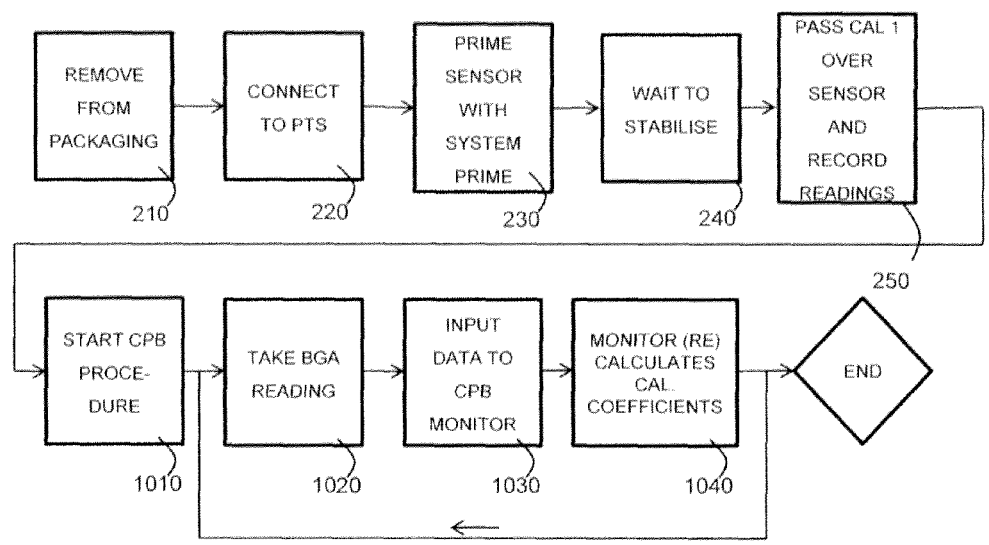
FIG. 10 depicts a flowchart of a method of correlating a sensor in accordance with yet another embodiment of the present invention.
Figure 11:
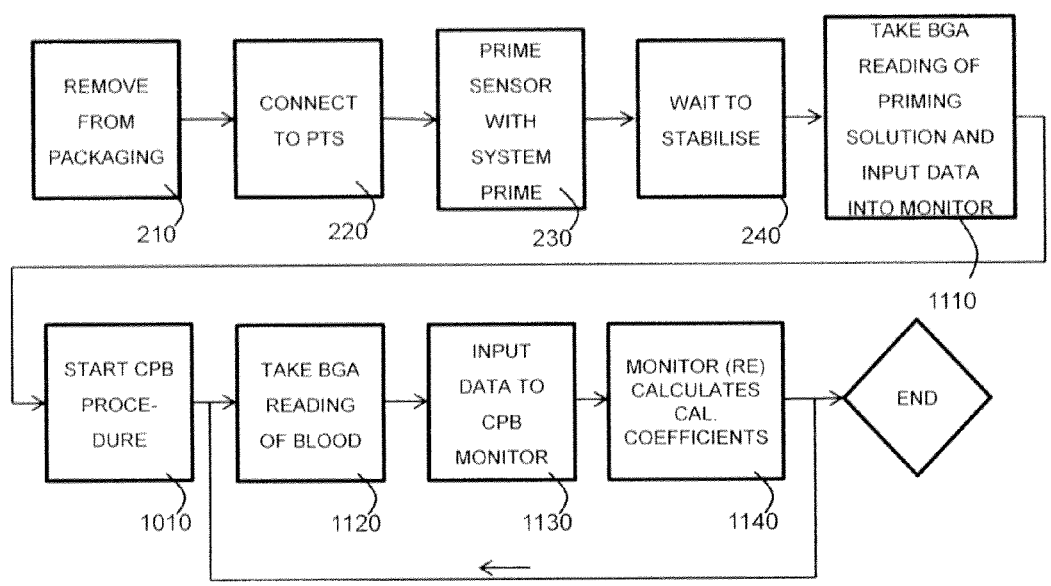
FIG. 11 depicts a flowchart of a method of correlating a sensor in accordance with yet another embodiment of the present invention.

FIGS. 10 and 11 depict embodiments of a method of calibrating a sensor for measuring an analyte in a patient monitoring system in accordance with yet another aspect of the present invention. In accordance with this method, at least one of the calibration fluids for calibrating the sensor has an initially unknown concentration of the analyte of interest. For example, as shown in FIG. 10, a sensor may be stabilised and subsequently exposed to a first calibration fluid in any suitable way, e.g. by means of the steps 210-250 of the known method depicted in FIG. 2.

An important difference, however, is that the concentration of the analyte of interest in the first calibration fluid administered in step 250 is unknown. In accordance with the present invention, the concentration of the analyte of interest is subsequently determined in an external analyser, after which the concentration determined by the external analyser is fed back to the sensor, thus facilitating the calculation of the calibration constants of the sensor.

This is particularly useful in a CPB procedure. To this end, a CPB procedure is started in step 1010 following the calibration measurement of the sensor in step 250, after which the calibration fluid is transferred to a blood gas and electrolyte analyser (BGA) in step 1020. The relevant results of the BGA are fed back to the sensor in step 1030, or more precisely, to the control means controlling the sensor, e.g. a monitor coupled to the sensor, after which the calibration coefficients are calculated in step 1040. This is particularly advantageous if the calibration fluid used in step 250 is the patient's blood, because no separate calibration fluid has to be used, thus reducing the time required for calibrating the sensor. The same procedure may be used for recalibrating the sensor when required.

The calibration method of FIG. 10 may be extended to a two-point calibration method, in which at least one of the fluids has an unknown concentration. This is shown in FIG.

11. In this embodiment, the sensor is stabilised as previously explained, after which a calibration first fluid having a first concentration of the analyte of interest is provided in step 1110. This concentration may be an unknown concentration. This fluid may be the priming fluid. The sensor measures the analyte concentration, and, in case of an unknown concentration, the external analyser, e.g. a BGA, determined the actual concentration of the analyte of interest. Next, the CPB procedure is started in step 1010, after which the sensor takes a measurement of the concentration of the analyte of interest in the patient's blood in step 1120. This concentration may also be an unknown concentration, in which case this concentration is also determined in the external analyser, e.g. the BGA. The data from the external analyser is fed back to the sensor in step 1130, after which the sensor calculates the calibration coefficients from the concentrations measured by the sensor, e.g. the signal strengths produced by the sensor, and the one or more concentrations determined by the external analyser.

It should be noted that the above-mentioned embodiments illustrate rather than limit the invention, and that those skilled in the art will be able to design many alternative embodiments without departing from the scope of the appended claims. In the claims, any reference signs placed between parentheses shall not be construed as limiting the claim. The word "comprising" does not exclude the presence of elements or steps other than those listed in a claim. The word "a" or "an" preceding an element does not exclude the presence of a plurality of such elements. The mere fact that certain measures are recited in mutually different dependent claims does not indicate that a combination of these measures cannot be used to advantage.

The invention claimed is:

1. A method of calibrating a sensor for measuring an analyte in a patient monitoring system, the method comprising:
    calculating a predictable sensor drift;
    calibrating the sensor using at least one calibration fluid;
    periodically updating the sensor calibration coefficients using the predicted sensor drift only,
        providing the sensor with a first fluid comprising a predetermined concentration of an analyte;
        performing a first measurement of the analyte concentration in the first fluid with the sensor;
        providing the sensor with a further fluid comprising a further predetermined concentration of an analyte;
        performing at least one additional measurement of the further analyte concentration in the further fluid with the sensor after a predetermined time period;
    wherein the step of calculating the predictable sensor drift comprises calculating said drift from the difference between the first measured analyte concentration and the further measured analyte concentration,
    wherein the patient monitoring system comprises means for adjusting a gas concentration in the system, and wherein the analyte is said gas, the method further comprising:
    maintaining a well-defined concentration of the gas in the first fluid with said means for adjusting a gas concentration during the first measurement and the further measurement,
    wherein one of the first fluid and the further fluid comprises the patient's blood.

2. A method as claimed in claim 1, wherein the gas comprises at least one of oxygen and carbon dioxide.

3. A method as claimed in claim 1, wherein the sensor comprises a means for altering the analyte concentration, and wherein the step of calculating the predictable drift comprises determining said drift based on a difference between the first measurement and the second measurement and a deviation of said difference from a predicted difference based on the known analyte consumption rate of said altering means.

4. A method as claimed in claim 1, wherein the first fluid and the further fluid are the same fluid.

5. A method as claimed in claim 4, wherein the sensor is arranged to determine the analyte concentration in a flowing sample, the method further comprising the step of maintaining the first fluid stationary over the sensor during a time period including the first measurement and the further measurement.

6. A method as claimed in claim 4, further comprising the step of stabilising the sensor with a priming fluid, said priming fluid comprising a first predetermined concentration of the analyte, and wherein:
    the first fluid comprises the priming fluid; and
    the first analyte concentration and the further analyte concentration are determined during said stabilising.

7. A method as claimed in claim 1 or 4 wherein the step of calculating a predictable sensor drift is performed during manufacturing of the sensor.

8. A method as claimed in claim 7, further comprising adjusting the predictable sensor drift based on said sensor calibration.

* * * * *

UNITED STATES PATENT AND TRADEMARK OFFICE
CERTIFICATE OF CORRECTION

| | |
|---|---|
| PATENT NO. | : 8,869,585 B2 |
| APPLICATION NO. | : 12/918311 |
| DATED | : October 28, 2014 |
| INVENTOR(S) | : Gavin Troughton and Peter Laitenberger |

It is certified that error appears in the above-identified patent and that said Letters Patent is hereby corrected as shown below:

On the Title Page, in Item [56] under References Cited, U.S. Patent Documents, Page 2, please delete "7,221,567 5/2007 Otsuki et al." and insert --4,221,567 9/1980 Clark et al--.

Signed and Sealed this
Fourteenth Day of April, 2015

Michelle K. Lee
*Director of the United States Patent and Trademark Office*